United States Patent
Almering et al.

(10) Patent No.: US 11,932,597 B2
(45) Date of Patent: Mar. 19, 2024

(54) CONVERTING ISOBUTANE AND REFINERY C4S TO PROPYLENE

(71) Applicant: LUMMUS TECHNOLOGY LLC, Houston, TX (US)

(72) Inventors: Martinus J. Almering, Houston, TX (US); Kerman N. Dukandar, Houston, TX (US); Oliver Chen, Houston, TX (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 0 days.

(21) Appl. No.: 18/181,860

(22) Filed: Mar. 10, 2023

(65) Prior Publication Data

US 2023/0286886 A1 Sep. 14, 2023

Related U.S. Application Data

(60) Provisional application No. 63/269,141, filed on Mar. 10, 2022.

(51) Int. Cl.
*C07C 6/04* (2006.01)
*C07C 5/25* (2006.01)
(Continued)

(52) U.S. Cl.
CPC .............. *C07C 6/04* (2013.01); *C07C 5/25* (2013.01); *C07C 5/2506* (2013.01); *C07C 5/27* (2013.01); *C07C 5/2702* (2013.01); *C07C 5/41* (2013.01)

(58) Field of Classification Search
CPC ........... C07C 6/04; C07C 5/25; C07C 5/2506; C07C 5/27; C07C 5/270241
See application file for complete search history.

(56) References Cited

U.S. PATENT DOCUMENTS 6,872,862 B2  3/2005  Bridges et al.
6,977,318 B2  12/2005  Bridges
(Continued)

FOREIGN PATENT DOCUMENTS

| CN | 112759500 A | 5/2021 |
| TW | 201038525 A | 11/2010 |
| WO | 2010077263 A2 | 7/2010 |

OTHER PUBLICATIONS

International Search Report issued in Application No. PCT/US2023/015008, dated Jun. 28, 2023 (5 pages).
(Continued)

*Primary Examiner* — In Suk C Bullock
*Assistant Examiner* — Jason Y Chong
(74) *Attorney, Agent, or Firm* — Osha Bergman Watanabe & Burton LLP

(57) ABSTRACT

A process for converting isobutane to propylene. The process including dehydrogenating isobutane to produce a mixed product stream comprising isobutane and isobutene, skeletal isomerizing the mixed product stream comprising isobutane and isobutene to convert isobutene to n-butenes including 1-butene and 2-butenes and to recover a skeletal isomerization reaction product comprising isobutane, isobutene, butadiene, 1-butene, and 2-butenes. The process further including fractionating the skeletal isomerization reaction product, isomerizing the 1-butene contained therein to 2-butenes, recovering an overhead fraction comprising isobutane, a side draw fraction comprising isobutane and isobutene, and a bottoms fraction comprising 2-butenes, and combining the bottoms fraction with ethylene and converting the ethylene and 2-butenes to produce a reaction effluent comprising propylene.

19 Claims, 2 Drawing Sheets

(51) Int. Cl.
    *C07C 5/27*           (2006.01)
    *C07C 5/41*           (2006.01)

(56) References Cited

U.S. PATENT DOCUMENTS

| | | |
|---|---|---|
| 7,074,976 B2 | 7/2006 | Powers et al. |
| 8,258,357 B2 | 9/2012 | Dukandar et al. |
| 9,725,380 B2 | 8/2017 | Fridman et al. |
| 2004/0192994 A1* | 9/2004 | Bridges .............. C07C 5/2556 585/664 |
| 2006/0089517 A1 | 4/2006 | Podrebarac et al. |
| 2012/0108864 A1 | 5/2012 | Gartside et al. |
| 2013/0102822 A1 | 4/2013 | Arnold et al. |
| 2017/0267795 A1 | 9/2017 | Kim et al. |

OTHER PUBLICATIONS

Written Opinion issued in Application No. PCT/US2023/015008, dated Jun. 28, 2023 (6 pages).
Office Action issued in Taiwan Application No. 112108929, dated Dec. 11, 2023 (10 pages).

* cited by examiner

CONVERTING ISOBUTANE AND REFINERY C4S TO PROPYLENE

FIELD OF THE DISCLOSURE

Embodiments of the present disclosure generally relate to processes and systems for conversion of isobutane and other refinery C4s to propylene. Such reaction schemes may include isomerization, metathesis, dehydrogenation and other reaction steps to attain the desired conversion of isobutane to propylene.

BACKGROUND

Various processes are known that produce isobutene. For example, dehydrogenation of isobutane may result in isobutene. Steam cracking and catalytic cracking of hydrocarbons may also produce C4 streams containing isobutene, among other saturated and unsaturated C4 hydrocarbons. Catalytic cracking is disclosed, for example, in U.S. Pat. No. 9,725,380.

In addition to discussing steam cracking of hydrocarbons, WO2010077263 discloses a process for producing propylene. The process includes skeletal isomerization of isobutene to produce normal butenes, followed by metathesis of the butenes with ethylene to form propylene. Skeletal isomerization and production of propylene are also described, for example, in U.S. Pat. Nos. 6,872,862, 6,977,318, and 7,074,976, among others.

SUMMARY OF THE CLAIMED EMBODIMENTS

In one aspect, embodiments disclosed herein relate to a system for converting isobutane to propylene. The system including a dehydrogenation unit for converting the isobutane to isobutene, and producing a mixed product stream comprising isobutane and isobutene and a skeletal isomerization unit for converting isobutene to n-butenes including 1-butene and 2-butenes via skeletal isomerization, and producing a skeletal isomerization product stream comprising isobutane, isobutene, 1-butene, and 2-butenes. The system further including a catalytic deisobutenizer unit for fractionating the skeletal isomerization product stream, converting the 1-butene to 2-butenes, and producing an overhead fraction comprising isobutane, a side draw fraction comprising isobutane and isobutene, and a bottoms fraction comprising 2-butenes, and an olefin conversion unit for converting the ethylene and the 2-butenes to propylene via metathesis, and to produce a propylene product stream.

In another aspect, embodiments disclosed herein relate to a process for converting isobutane to propylene. The process including dehydrogenating isobutane to produce a mixed product stream comprising isobutane and isobutene, skeletal isomerizing the mixed product stream comprising isobutane and isobutene to convert isobutene to n-butenes including 1-butene and 2-butenes and to recover a skeletal isomerization reaction product comprising isobutane, isobutene, 1-butene and 2-butenes. The process further including fractionating the skeletal isomerization reaction product, isomerizing the 1-butene contained therein to 2-butenes, recovering an overhead fraction comprising isobutane, a side draw fraction comprising isobutane and isobutene, and a bottoms fraction comprising 2-butenes, and combining the bottoms fraction with ethylene and converting the ethylene and 2-butenes to produce a reaction effluent comprising propylene.

In another aspect, embodiments disclosed herein relate to a process for converting mixed C4s to propylene. The process including skeletal isomerizing the mixed C4s comprising isobutane and isobutene to convert isobutene to n-butenes including 1-butene and 2-butenes and to recover a skeletal isomerization reaction product comprising isobutane, isobutene, 1-butene and 2-butenes. The process further including fractionating the skeletal isomerization reaction product, isomerizing the 1-butene contained therein to 2-butenes, and recovering an overhead fraction comprising isobutane, a side draw fraction comprising isobutane and isobutene, and a bottoms fraction comprising 2-butenes. The process further including combining the bottoms fraction with ethylene and converting the ethylene and 2-butenes to produce a reaction effluent comprising propylene, dehydrogenating the overhead fraction comprising isobutane to produce additional mixed C4s comprising isobutane and isobutene, and recycling the side draw fraction comprising isobutane and isobutene to the skeletal isomerizing step.

Other aspects and advantages will be apparent from the following description and the appended claims.

DETAILED DESCRIPTION

Figure 1:
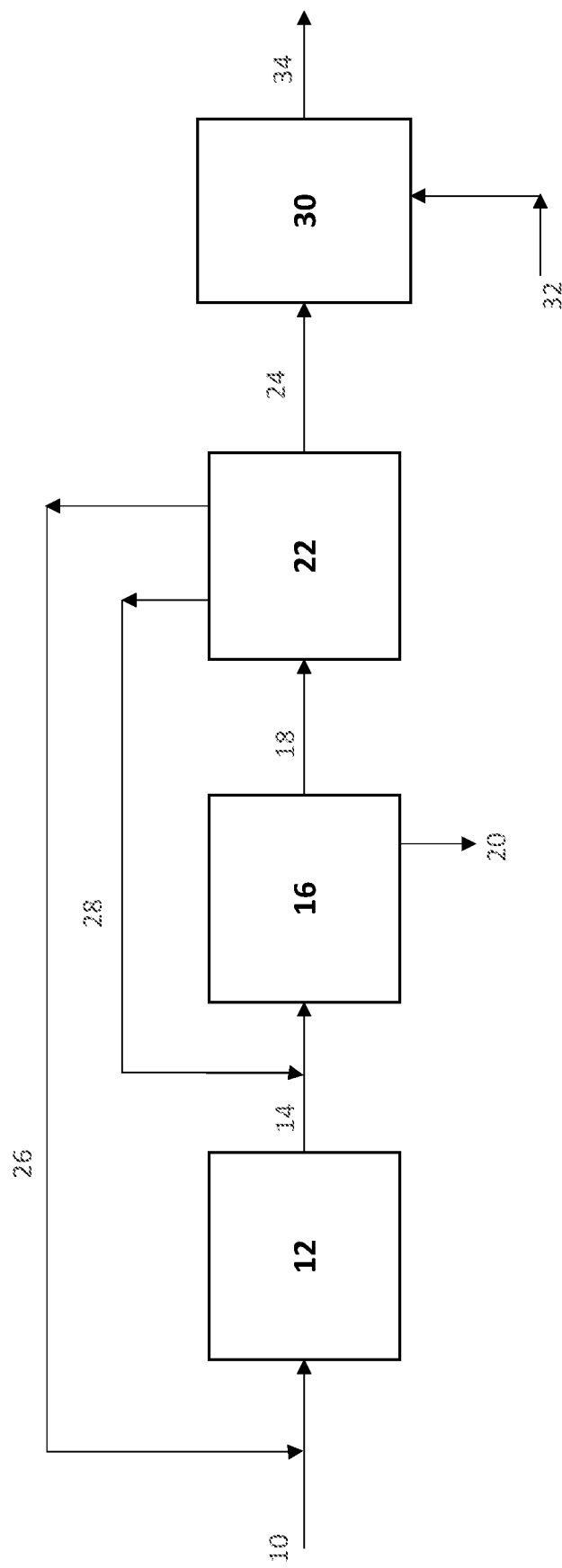
FIG. 1 illustrates a simplified process flow diagram of systems for converting isobutane to propylene according to one or more embodiments disclosed herein.

Embodiments herein are directed toward processes and systems that allow for an efficient conversion of isobutane to propylene. Embodiments herein are also directed toward processes and systems that allow for an efficient conversion of isobutane to polymerization grade propylene.

In general, the process configuration of embodiments herein includes four general unit operations. The first unit is a catalytic isobutane dehydrogenation unit producing a mixed isobutene/isobutane effluent from a mainly isobutane feed. The second unit is a C4 olefin skeletal isomerization unit which produces a mixed C4 olefin product from a mainly isobutene/isobutane mixture; a small amount of C5+ byproduct is produced as well. The third unit is a catalytic deisobutenizer producing an isobutane top product, a 2-butenes and n-butane bottoms, and a mixed isobutane/isobutene containing stream. The fourth unit is a unit for converting the 2-butenes to a desired end product; in some embodiments, the fourth unit is a metathesis unit that converts 2-butenes together with ethylene into propylene, while in other embodiments the fourth unit may be used for production of ethers, dimers, oligomers, or other useful end products or intermediates. In some embodiments, polymerization grade ethylene is used as a feedstock and polymerization grade propylene is recovered as a product. While described above with respect to four primary units, each unit may include reactors, heat exchangers, separators, feed treatment, internal recycles, and other processing or support equipment and features to achieve the desired conversion and products; while not all aspects of the unit operations are described in detail herein, one skilled in the art should appreciate the primary function of each respective unit based on the description herein.

The third unit, the catalytic deisobutenizer, contains hydroisomerization/selective hydrogenation catalyst and simultaneously converts 1-butene to 2-butenes while fractionating a mainly 2-butenes and n-butane into a bottom product stream. The liquid top product of the fractionator is a mostly isobutane containing product. A third main product is taken from the column as a mixed mostly isobutane and isobutene containing stream as well as a minority or small fraction of other components as may be dictated by column operating conditions. This side draw product can be either a liquid or a vapor and is drawn from the column intermediate, such as mid-way between, the top of the column and the feed location. Due to the concurrent fractionation of 2-butenes downwards and 1-butene upwards, multiple catalyst zones achieve a high conversion of 1-butene to 2-butenes past its normal equilibrium conversion as observed in single stage reactors. Overall, the catalytic deisobutenizer is combined with an isobutane purification top section, which uses the available reflux to concentrate isobutane as a high purity top product suitable for recycle to an upstream or downstream process, such as the isobutane dehydrogenation unit.

The side draw product, the mixed isobutane/isobutene containing stream, recovered from the catalytic deisobutenizer is fed into the second unit together with the effluent of the first unit. In other words, the feed to the skeletal isomerization unit is a mixture of isobutene and isobutane, including isobutene/isobutane as received from the first unit and isobutene and isobutane as received from the third unit. The top product of the catalytic deisobutenizer, being primarily isobutane, is fed back into the first unit, dehydrogenation, together with the fresh isobutane feed.

A small hydrogen stream is also fed to the catalytic deisobutenizer column to allow for the selective hydrogenation of multi-unsaturated C4 components (butadienes and/or acetylenes) as well as to keep the hydroisomerization/selective hydrogenation catalyst in the active form. A small unreacted hydrogen vent stream can be taken from the overhead system associated with the column.

The catalytic deisobutenizer column as described above can be physically split into two or more articulated fractionation sections in some embodiments. The articulated fractionation sections may include pumps allowing for liquid transfer between the sections and flow lines providing for vapor transfer between sections of the column. In some embodiments, the side draw product is removed as a vapor stream product intermediate the top and bottom sections of an articulated column, withdrawn from the vapors being transported from the top of the stripping section as it is being transported to the rectifying section. Hydrogen may be fed below the catalyst containing sections of the column or may be fed intermediate each of the catalyst containing distillation zones. The catalyst may be contained in the upper portion of the stripping section. The feed to the catalytic deisobutenizer may be fed below or intermediate the catalytic reactive distillation zones.

Further, in some embodiments, the third unit fractionation column can be fitted with a heat pump. The overhead system associated with the catalytic deisobutenizer may include a compressor to compress the overhead vapors, which then can be condensed at a higher temperature in the column reboiler vaporizing the column bottoms liquid. When used in various embodiments, this system replaces the requirement of an external heat source, such as condensing steam, in the reboiler and replaces it with a motive energy to drive the compressor with electrical current or motive high pressure steam. Such embodiments may result in a saving of total energy consumption of between 80% to 90% compared to columns using external heating and cooling sources.

Isobutane Dehydrogenation Unit

Feeds to the first unit, catalytic isobutane dehydrogenation, may comprise, consist essentially of, or consist of isobutane. A fresh isobutane feedstock may be provided from any number of sources, including fractionation of various C4-containing streams from a refinery, isobutane recovered from tertiary butyl alcohol dehydration or tertiary butyl ether decomposition, or isobutane from other various sources. The isobutane feedstock may be of a high purity, such as greater than 50 wt %, greater than 70 wt % isobutane, greater than 80 wt % isobutane, greater than 90 wt % isobutane, greater than 95 wt % isobutane, or greater than 98 or 99 wt % isobutane. The remainder of the feedstock may include additional hydrocarbons or inert diluents, such as nitrogen.

Additionally, as noted above, a recycle isobutane feedstock may be provided from the third unit, the catalytic deisobutenizer overheads. The deisobutenizer overheads may also be a high purity isobutane stream, and in some embodiments may contain greater than 98 wt % or greater than 99 wt % isobutane.

The total isobutane feed fed to the catalytic isobutane dehydrogenation may include both fresh isobutane from an upstream process, as well as recycle isobutane from the downstream catalytic deisobutenizer. A ratio of fresh isobutane to recycle (deisobutenizer) isobutane may vary, depending upon the conversion efficiency in the reactor, the amount of other refinery or isobutane containing C4 streams fed to the catalytic deisobutenizer, and other variables. In some embodiments, a ratio of fresh to recycle isobutane is in the range of 0.2:1 to 1:0.2, such as from 0.5:1 to 1:0.5.

The catalytic dehydrogenation may be an oxidative or non-oxidative dehydrogenation. Each of the respective dehydrogenation processes are known to those skilled in the art and will not be expanded upon here other than to note that various reactor types, catalysts, and configurations may be used, and operating conditions may be appropriately selected based on the reaction type, catalyst, and overall feed composition to achieve the desired conversion.

The effluent from the catalytic dehydrogenation reactors may then be separated to recover a mixed isobutane/isobutene stream. Other products from the isobutane dehydrogenation may include a hydrogen stream (resulting from the dehydrogenation), as well as small amounts of C1-C3 or C5+ byproducts. In some embodiments, a mixed C4 stream from the catalytic dehydrogenation unit or a mixed C4+ stream from the dehydrogenation unit may be fed to the second unit, the isobutene skeletal isomerization unit.

Skeletal Isomerization Unit

Feeds to the second unit may include the mixed C4 stream or a mixed C4+ stream from the catalytic dehydrogenation unit. Additionally, isobutene is provided in the form of an isobutene/isobutane mixture recovered from the downstream catalytic deisobutenizer.

Depending on the feedstock to the isobutane dehydrogenation unit, and the overall conversion in the isobutane dehydrogenation unit, a catalyst de-oiler may be present between the isobutane dehydrogenation unit and the skeletal isomerization unit. The purpose of the catalyst de-oiler is to remove at least a portion of the undesired C5+ byproducts as well as to hydrogenate at least a portion of any residual 1,3-butadiene formed in the dehydrogenation unit. The catalytic de-oiler thus may serve to prepare the dehydrogenation effluent for the skeletal isomerization unit.

In the skeletal isomerization unit, the isobutene feeds are mixed and vaporized. In some embodiments, isobutene is provided from dehydrogenation as a liquid and isobutene is fed as a vapor, such as a vapor side draw recovered from the catalytic deisobutenizer. In such embodiments, the stream from dehydrogenation may be vaporized and then mixed with the vapor from the catalytic deisobutenizer. Where the side draw is liquid, the combined streams may be vaporized. The combined vapor stream may be heated, such as via a reactor feed/effluent heat exchanger, and then further heated to reaction temperature and sent to the reactors.

The skeletal isomerization of isobutene to linear butenes (1-butenes and 2-butenes) may be performed in a vapor phase reactor over a skeletal isomerization catalyst. Olefin skeletal isomerization processes are known to those skilled in the art and will not be expanded upon here other than to note that various reactor types, catalysts, and configurations may be used, and operating conditions may be appropriately selected based on the reaction type, catalyst, and overall feed composition to achieve the desired conversion of isobutene to normal butenes. Byproducts from the skeletal isomerization may include C3− and/or C5+ hydrocarbons.

The effluent from the skeletal isomerization reactors may then be separated to recover a mixed C4 stream, including unreacted isobutane, unreacted isobutene, normal butenes (1-butenes and 2-butenes). The recovered C4 stream may include lighter hydrocarbon byproducts in some embodiments; in other embodiments, the separations may include recovering a C3− hydrocarbon stream. The separations may also produce a fraction including C5 and heavier hydrocarbon byproducts. The C5+ byproducts may be recovered as a fuel fraction or gasoline blending fraction in some embodiments. The C4 effluent from the isomerization reaction zone may then be fed to the third unit, the catalytic deisobutenizer. In some embodiments, at least a portion (e.g., from 40 wt % to 99.9 wt % of the C5+ components, such as 75 wt % to 99 wt % of the C5+ components, may be removed from the skeletal isomerization effluent before forwarding of the C4 effluent from the skeletal isomerization zone to the catalytic deisobutenizer. The resulting C4 effluent, in some embodiments, may include less than 1 wt % C5+ hydrocarbons, for example.

Various skeletal isomerization technologies and methods exists. Most use an acidic catalyst and operate at a temperature range of 250 to 450° C. where the chemical equilibrium provides enough drive towards n-butenes. These methods also operate between 1.0 and 2.5 bara or use a dilution medium to lower the partial pressure of olefin in order to limit dimerization and thus improve selectivity. The resulting ratio of n-butenes to isobutene in the reactor effluent varies between 0.70 and 1.2.

Catalytic Deisobutenizer Unit

The mixed C4s from the skeletal isomerization unit are fed to a catalytic deisobutenizer. In the deisobutenizer, the C4 stream is further processed using positional isomerization and hydrogenation catalysts, along with a hydrogen feed, converting 1-butene to 2-butenes and selectively hydrogenating any butadiene that may be present from upstream processing in the dehydrogenation and skeletal isomerization units. Concurrent fractionation results in three C4-product streams, including a 2-butenes and n-butane bottoms product, an isobutane overhead product, and a mixed isobutene/isobutane side draw. The isobutane overhead product may be recycled to isobutane dehydrogenation, if desired. Similarly, the mixed isobutene/isobutane side draw may be fed to the skeletal isomerization unit for continued conversion of the isobutene to n-butenes.

In some embodiments, a mixed C4 stream may additionally be fed to the catalytic deisobutenizer for separation along with the isomerization effluent. Mixed C4 streams that may be fed to the catalytic deisobutenizer may include, for example, C4 streams recovered from various refinery operations, including catalytic cracking, steam cracking, or dimerization, among others. The C4 streams in some embodiments may include Raffinate-1 streams or Raffinate-2 streams, for example, following butadiene recovery. In some embodiments, a mixed C4 stream may be provided from a fractionator separating a refinery C3/C4 olefin containing stream. In one or more embodiments, the mixed C4 stream may be fed to a hydroisomerization reactor for conversion of 1-butene to 2-butenes followed by a deisobutenizer for separation of the mixed C4s from the remaining hydrocarbons.

As noted above, the product streams from the catalytic deisobutenizer may include an overhead isobutane fraction, a side draw isobutene/isobutane mixture, and a bottoms fraction including the desired 2-butenes positional isomerization product. A hydrogen containing vent gas may also be recovered. The side draw may be located within the column at an appropriate elevation to recover an isobutane/isobutene stream having a ratio of isobutane to isobutene in the range from 1:2 to 2:1, such as 1:1.5 to 1.5 to 1, or 0.9:1 to 1:0.9 for example. The side draw may be located above the catalytic distillation reaction zone, and the feed may be located below the catalytic distillation reaction zone, providing for a side draw containing a relatively low amount of n-butenes, such that a stream containing greater than 80%, greater than 95% or greater than 98% isobutane/isobutene may be provided as a recycle feed to the skeletal isomerization unit. Sufficient trays and height to the column may also be provided to result in an isobutane overhead stream containing primarily isobutane, such as greater than 95% or greater than 98% isobutane, suitable for recycle into the upstream isobutane dehydrogenation unit. The bottoms product from the catalytic deisobutenizer, which includes 2-butenes, is then fed to the fourth unit, a metathesis reaction zone.

Operating conditions in the catalytic deisobutenizer may be in the range of 25 to 85° C. and a pressure in the range of 3.5 to 7.5 barg. Additionally, the catalytic deisobutenizer may be operated with a reflux ratio in the range of 0.5:1 to 33:1.

Olefins Conversion Unit (Metathesis Unit)

In this unit, the n-butenes (2-butenes) from the catalytic deisobutenizer bottoms are combined with fresh and/or recycle ethylene and fed to the metathesis reactor(s) for conversion therein to propylene (2-butenes+ethylene→two propylene molecules). In some embodiments, the feeds may be treated to remove trace impurities before being fed to the metathesis reactors, which can accept both 1-butenes and 2-butenes, such as where the metathesis unit also includes an isomerization catalyst to catalytically isomerize 1-butene to 2-butenes upstream of or within the metathesis reactors. The ethylene feed, in some embodiments, is a polymerization grade ethylene stream containing greater than 99.5 wt % ethylene.

Feed to the metathesis reactors may be heated upstream of the reactors, such as by using reactor feed/effluent heat exchangers, heaters, or other indirect heat exchange to arrive at the desired feed temperature. Following conversion in the metathesis reaction zone, the effluent from the reactors may be fed to a recovery section for separation of the effluent into a recycle ethylene stream, a recycle butenes stream, and a propylene stream. In some embodiments, the propylene product may be a polymer grade propylene stream (greater than 99 wt % propylene, greater than 99.8 wt % propylene, or greater than 99.9 wt % propylene in some embodiments). A C4+ byproduct stream may also be recovered. In some embodiments, an ethylene-rich vent stream recovered may be sent to an upstream processing unit for ethylene recovery. In other embodiments, a C3− stream recovered from the skeletal isomerization unit may be fed to the olefin conversion unit recovery section for processing and recovery of the C3− hydrocarbons along with the respective product, recycle, and purge fractions.

Processes for olefin conversion via metathesis are known to those skilled in the art and will not be expanded upon here other than to note that various reactor types, catalysts, and configurations may be used, and operating conditions may be appropriately selected based on the reaction type, catalyst, and overall feed composition to achieve the desired conversion of normal butenes and ethylene to propylene.

Additional 2-Butenes Processing

As noted above, the 2-butenes containing bottoms product from the catalytic deisobutenizer may be fed to the olefin conversion unit to produce propylene. In other embodiments, the 2-butenes containing bottoms product from the catalytic deisobutenizer, or a portion thereof, may be fed to a process unit for converting 2-butenes to sec-butyl alcohol (SBA) and/or methyl ethyl ketone (MEK).

Referring now to FIG. 1, a simplified block flow diagram of processes according to embodiments herein is illustrated. An isobutane containing stream 10 is fed to an isobutane dehydrogenation unit 12, converting the isobutane to isobutene therein. A dehydrogenation reaction product 14 comprising isobutane and isobutene is recovered from the isobutane dehydrogenation unit 12 and fed to a skeletal isomerization unit 16 for conversion of the isobutene to n-butenes. A skeletal isomerization product 18, including unreacted isobutane, unreacted isobutene, n-butenes and n-butane, is recovered from the skeletal isomerization unit 16; a C5+ hydrocarbon byproduct stream 20 may also be recovered from the skeletal isomerization unit 16. In other embodiments, a C3− hydrocarbon stream (not illustrated) may be recovered from the skeletal isomerization unit 16.

The skeletal isomerization product 18 is then fed to a catalytic deisobutenizer 22 to selectively hydrogenate any butadiene present in the skeletal isomerization product and to convert 1-butene to 2-butenes via positional isomerization, while concurrently (simultaneously) fractionating the reaction products and other feed components to produce a bottoms 2-butenes containing stream 24, an overheads isobutane product 26, and a side draw 28 containing both isobutane and isobutene.

The resulting isobutane/isobutene side draw 28 may be fed to the skeletal isomerization unit 16 for continued conversion of the isobutene to n-butenes. The overhead isobutane stream 26 may be fed to the dehydrogenation unit for continued conversion of the isobutane to isobutene. The bottoms 2-butenes stream 24 is fed to a downstream olefin conversion unit 30 for conversion of the 2-butenes to desired end products or desired intermediate products. In some embodiments, for example, the bottoms 2-butenes stream 24 may be mixed with ethylene 32 and reacted in the downstream olefin conversion unit 30 over a metathesis catalyst to produce a high purity propylene product stream 34.

Figure 2:
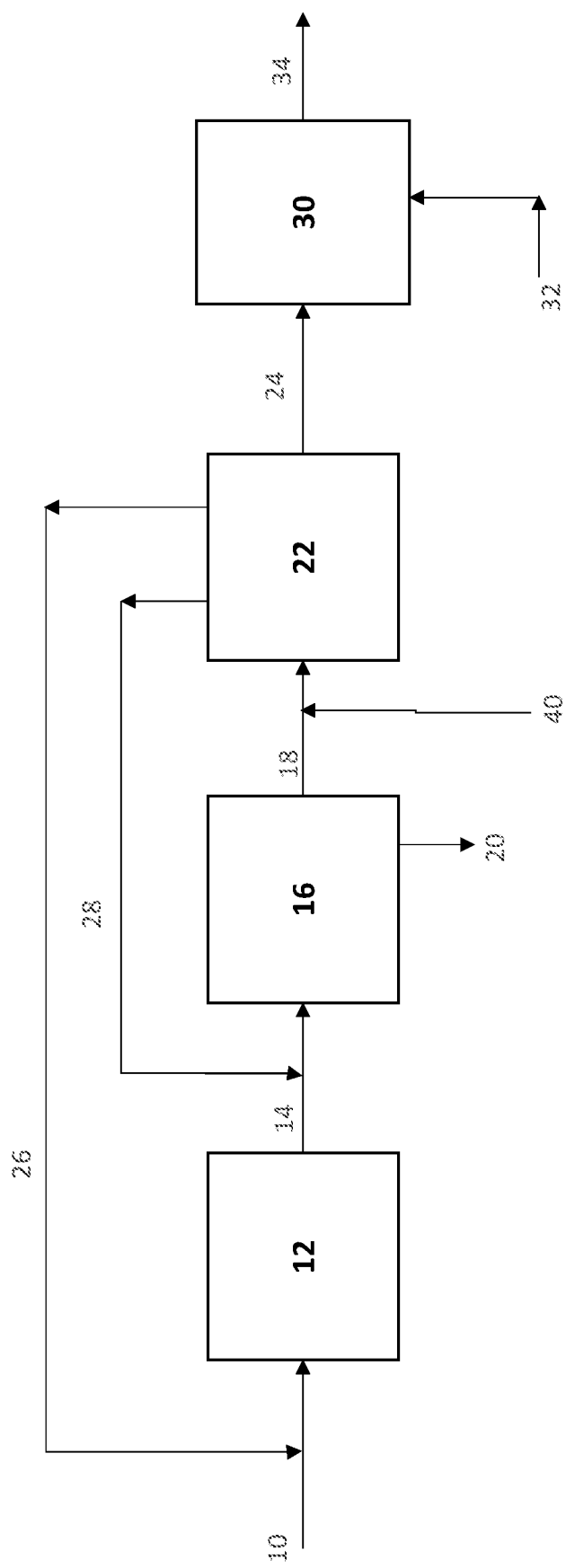
FIG. 2 illustrates a simplified process flow diagram of systems for converting isobutane to propylene according to one or more embodiments disclosed herein.

Referring now to FIG. 2, a simplified block flow diagram of processes according to embodiments herein is illustrated, where like numerals represent like parts. In this embodiment, the feedstock isobutane stream 10 is processed similar to FIG. 1. However, in this embodiment, an additional source of C4 olefins is provided via flow line 40, the additional C4s being fed to the catalytic deisobutenizer 22. The additional source of C4 olefins may include normal butenes, isobutenes, or both, as well as isobutane and normal butane, depending on the feed source. The C4 components are processed along with the skeletal isomerization C4 product to recover the overhead isobutane 26, side draw isobutene/isobutane stream 28, as well as the 2-butenes containing bottoms stream 24 used for conversion to propylene in olefin conversion unit 30.

In one or more embodiments, the additional C4 olefins stream 40 may be the primary feedstock to the process, with little or no isobutane being fed to the process by isobutane stream 10. In such embodiments, the isobutane dehydrogenation unit 12 and skeletal isomerization unit 16 may be substantially fed by isobutane recycle stream 26 and isobutane/isobutene recycle stream 28. In these embodiments, the operational flexibility may allow for the process and system to facilitate the conversion of C4 feedstocks from various sources including primarily isobutane stream 10, primarily C4 olefin stream 40, or any mixture thereof.

As described above, embodiments herein provide for the efficient conversion of isobutane to propylene. Advantageously, embodiments herein utilize a catalytic deisobutenizer to react and separate mixed C4 feedstocks into an isobutane stream of a high purity suitable for feed to a dehydrogenation unit, a mixed isobutane/isobutene stream suitable for feed to an olefin skeletal isomerization unit, as well as a 2-butenes stream suitable for feed to an olefin conversion unit for production of a high purity propylene stream. Embodiments herein may convert a high percentage of the isobutane to propylene, such as greater than 90% or greater than 95% of the feed isobutane being converted to propylene, on a molar basis. Converting essentially all of the isobutane to higher value end products, such as polymer grade propylene, will be economically favorable for many refiners and other operators.

Unless defined otherwise, all technical and scientific terms used have the same meaning as commonly understood by one of ordinary skill in the art to which these systems, apparatuses, methods, processes and compositions belong.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed as new and desired to be protected by Letters Patent is:

1. A system for converting isobutane to propylene, the system comprising:
   a dehydrogenation unit configured to receive an isobutane containing stream, convert isobutane to isobutene, and produce a mixed product stream comprising isobutane and isobutene;
   a skeletal isomerization unit configured to receive the mixed product stream, convert isobutene to n-butenes including 1-butene and 2-butenes via skeletal isomerization, and produce a skeletal isomerization product stream comprising isobutane, isobutene, 1-butene, and 2-butenes;
   a catalytic deisobutenizer unit configured to concurrently:
      receive the skeletal isomerization product stream,
      fractionate the skeletal isomerization product stream,
      convert the 1-butene to 2-butenes, and
      produce an overhead fraction comprising isobutane, a side draw fraction comprising isobutane and isobutene, and a bottoms fraction comprising 2-butenes; and
   an olefin conversion unit configured to receive an ethylene stream and the bottoms fraction comprising 2-butenes, convert the ethylene and the 2-butenes to propylene via metathesis, and to produce a propylene product stream.

2. The system of claim 1, wherein the propylene product stream is a polymer grade propylene stream.

3. The system of claim 1, wherein the catalytic deisobutenizer unit is further configured to receive a hydrogen stream and contains a hydrogenation catalyst suitable to selectively hydrogenate any butadiene received.

4. The system of claim 1, wherein the catalytic deisobutenizer unit is further configured to receive a mixed C4 stream containing isobutene, isobutane, n-butenes, and n-butane.

5. The system of claim 1, further comprising a first flow line for feeding the overhead fraction comprising isobutane to the dehydrogenation unit.

6. The system of claim 1, further comprising a second flow line for feeding the side draw fraction comprising isobutane and isobutene to the skeletal isomerization unit.

7. The system of claim 1, wherein the catalytic deisobutenizer unit comprises a feed tray, a side draw tray, and a catalytic distillation zone, and wherein the feed tray is located below the catalytic distillation zone and the side draw tray is located above the catalytic distillation zone.

8. The system of claim 1, wherein the skeletal isomerization unit includes a separation system configured to recover 40 to 99.99 wt % of C5+ hydrocarbon byproducts.

9. A process for converting isobutane to propylene, the process comprising:
   dehydrogenating an isobutane-containing stream to produce a mixed product stream comprising isobutane and isobutene;
   skeletal isomerizing the mixed product stream comprising isobutane and isobutene to convert isobutene to n-butenes including 1-butene and 2-butenes to recover a skeletal isomerization reaction product comprising isobutane, isobutene, butadiene, 1-butene, and 2-butenes;
   concurrently:
      fractionating the skeletal isomerization reaction product,
      isomerizing the 1-butene contained therein to 2-butenes, and
      recovering an overhead fraction comprising isobutane, a side draw fraction comprising isobutane and isobutene, and a bottoms fraction comprising 2-butenes; and
   combining the bottoms fraction with an ethylene stream and converting the ethylene and 2-butenes to produce a reaction effluent comprising propylene.

10. The process of claim 9, further comprising separating the reaction effluent to recover a polymerization grade propylene product stream.

11. The process of claim 9 further comprising feeding the overhead stream comprising isobutane to the dehydrogenating step.

12. The process of claim 9, further comprising feeding the side draw comprising isobutane and isobutene to the skeletal isomerizing step.

13. The process of claim 9, wherein the concurrently fractionating and isomerizing further comprises concurrently hydrogenating butadiene.

14. The process of claim 9, further comprising feeding a mixed C4 stream comprising isobutane, isobutene, n-butane, and n-butenes to the concurrently fractionating and isomerizing step.

15. The process of claim 9, wherein the skeletal isomerization reaction product comprises less than 1 wt % C5+ hydrocarbons.

16. The process of claim 9, wherein the overhead fraction comprises greater than 95 wt % isobutane.

17. The process of claim 9, wherein the side draw fraction comprises greater than 95 wt % isobutane and isobutene.

18. The process of claim 17, wherein the side draw fraction comprises isobutane and isobutene at a ratio of isobutane to isobutene in a range from 1:1.5 to 1.5:1.

19. A process for converting mixed C4 hydrocarbons to propylene, the process comprising:
   skeletal isomerizing the mixed C4 hydrocarbons comprising isobutane and isobutene to convert isobutene to n-butenes including 1-butene and 2-butenes and to recover a skeletal isomerization reaction product comprising isobutane, isobutene, butadiene, 1-butene, and 2-butenes;
   concurrently:
   fractionating the skeletal isomerization reaction product,
   isomerizing the 1-butene contained therein to 2-butenes, and
   recovering an overhead fraction comprising isobutane, a side draw fraction comprising isobutane and isobutene, and a bottoms fraction comprising 2-butenes;
   combining the bottoms fraction with ethylene and converting the ethylene and 2-butenes to produce a reaction effluent comprising propylene;
   dehydrogenating the overhead fraction comprising isobutane to produce additional mixed C4 hydrocarbons comprising isobutane and isobutene; and
   recycling the side draw fraction comprising isobutane and isobutene to the skeletal isomerizing step.

* * * * *